(12) United States Patent
Binderman et al.

(10) Patent No.: US 9,782,240 B2
(45) Date of Patent: Oct. 10, 2017

(54) SUB-PERIOSTEAL EXTENSION FOR A DENTAL IMPLANT

(71) Applicant: Medintal Ltd., Tel-Aviv (IL)

(72) Inventors: Itzhak Binderman, Tel-Aviv (IL); Avinoam Yaffe, Mevasseret Zion (IL); Gideon Hallel, Sitriya (IL); Amit Binderman, Cresskill, NJ (US)

(73) Assignee: MEDINTAL LTD., Tel-Aviv (IL)

( * ) Notice: Subject to any disclaimer, the term of this patent is extended or adjusted under 35 U.S.C. 154(b) by 0 days.

(21) Appl. No.: 14/231,782

(22) Filed: Apr. 1, 2014

(65) Prior Publication Data

US 2015/0125818 A1    May 7, 2015

Related U.S. Application Data

(60) Provisional application No. 61/898,508, filed on Nov. 1, 2013.

(51) Int. Cl.
*A61C 8/00*    (2006.01)

(52) U.S. Cl.
CPC ............ *A61C 8/0078* (2013.01); *A61C 8/005* (2013.01); *A61C 8/0013* (2013.01); *A61C 8/0024* (2013.01); *A61C 8/0068* (2013.01); *A61C 8/0074* (2013.01); *A61C 8/0075* (2013.01); *A61C 8/0031* (2013.01)

(58) Field of Classification Search
CPC ....... A61C 8/00; A61C 8/0006; A61C 8/0018; A61C 8/0031
USPC ................................................ 433/172–176
See application file for complete search history.

(56) References Cited

U.S. PATENT DOCUMENTS

| 4,086,701 A | * | 5/1978 | Kawahara ................ A61C 8/00 433/174 |
| 4,259,072 A | * | 3/1981 | Hirabayashi ......... A61C 8/0012 433/173 |
| 4,531,916 A | | 7/1985 | Scantlebury et al. |

(Continued)

FOREIGN PATENT DOCUMENTS

| WO | WO 2008/004220 | 1/2008 |
| WO | WO 2015/063760 | 5/2015 |

OTHER PUBLICATIONS

International Search Report and the Written Opinion Dated Mar. 3, 2015 From the International Searching Authority Re. Application No. PCT/IL2014/050928.

(Continued)

*Primary Examiner* — Matthew Nelson
(74) *Attorney, Agent, or Firm* — Vorys, Sater, Seymour & Pease LLP

(57) ABSTRACT

A dental implant comprising a subperiosteal extension, said extension extending radially beyond a radius of a post of said dental implant. A device for mounting onto a dental implant configured to extend said dental implant to comprise a subperiosteal extension, said device extending radially beyond an interface between bone and said dental implant. A method of implanting a dental implant comprising elevating a mucoperiosteal flap at site of implantation, drilling a hole for inserting a dental implant comprising a subperiosteal extension, inserting said dental implant, and covering said subperiosteal extension with said mucoperiosteal flap. Related apparatus and methods are also described.

14 Claims, 10 Drawing Sheets

(56) References Cited

U.S. PATENT DOCUMENTS

| | | | | |
|---|---|---|---|---|
| 4,702,697 A * | 10/1987 | Linkow | ............... | A61C 8/0031 433/173 |
| 4,728,331 A * | 3/1988 | Russier | ............... | A61C 8/0006 106/35 |
| 4,846,683 A * | 7/1989 | Lazzara | ............... | A61C 8/0048 433/173 |
| 5,419,701 A * | 5/1995 | Propper | ............... | A61C 8/0009 433/173 |
| 5,437,551 A | 8/1995 | Chalifoux | | |
| 5,683,249 A * | 11/1997 | Ibsen | ............... | A61C 8/0012 433/173 |
| 5,906,489 A * | 5/1999 | Khazzam | ............ | A61C 8/0022 433/173 |
| 5,944,526 A * | 8/1999 | Liu | ................ | A61C 8/001 433/176 |
| 6,394,807 B2 * | 5/2002 | Robinson | ............ | A61C 8/0006 433/173 |
| 2001/0005577 A1 * | 6/2001 | Devincenzo | ......... | A61C 8/0022 433/173 |
| 2006/0154204 A1 * | 7/2006 | Reggie | ................ | A61C 8/001 433/173 |
| 2007/0134623 A1 * | 6/2007 | Essiger | ............ | A61B 17/8038 433/173 |
| 2009/0117519 A1 * | 5/2009 | Freilich | ................ | A61B 17/68 433/173 |
| 2009/0226857 A1 * | 9/2009 | Grant | ................... | A61C 8/0048 433/174 |
| 2009/0291415 A1 * | 11/2009 | Binderman | ......... | A61C 8/0016 433/200.1 |
| 2012/0100502 A1 * | 4/2012 | Djordjevic | ............ | A61C 8/001 433/173 |
| 2012/0214127 A1 | 8/2012 | Drapeau et al. | | |

OTHER PUBLICATIONS

Consolaro et al. "Intrusive Mechanics Generates Inclination Forces and Orthopedic Stimulus Followed by Simultaneous Dental Repositioning and Bone Remodelling or Intrusion Forces Are Not Applied in Intrusive Mechanics, But Intrusive Effects Are Still Obtained", Dental Press Journal of Orthodontic, 16(5): Sep. 20-29,-Oct. 2011.

Dwek "The Periosteum: What Is It, Where Is It, and What Mimics It in Its Absence?", Skeletal Radiology, 39(4): 319-323, 2010.

Knothe Tate et al. "Surgical Membranes as Directional Delivery Devices to Generate Tissue: Testing in an Ovine Critical Sized Defect Model", PLoS ONE, 6(12): e28702-1-e28702-9, Dec. 12, 2011.

* cited by examiner

SUB-PERIOSTEAL EXTENSION FOR A DENTAL IMPLANT

RELATED APPLICATION

This application claims the benefit of priority under 35 USC 119(e) of U.S. Provisional Patent Application No. 61/898,508 filed Nov. 1, 2013, the contents of which are incorporated herein by reference in their entirety.

FIELD AND BACKGROUND OF THE INVENTION

The present invention, in some embodiments thereof, relates to a dental implant and, more particularly, but not exclusively, to a dental implant with a sub-periosteal extension and to a sub-periosteal extension for a dental implant.

A Tooth Implant Procedure

There are many artificial tooth replacement techniques. Single tooth replacements using dental implants, and specifically osseo-integrated implants, are among the more successful dental procedures performed. The dental industry continuously strives to improve the functionality of the osseo-integrated implant with respect to osseous and gum preservation and aesthetics.

A typical dental implant includes a titanium post, which is screwed and/or fixed into a jawbone and functions as a tooth root substitute. Typically, a dentist surgically embeds the post into the patient's jawbone in place of a missing tooth, typically at a level of bone crest. A prosthetic abutment is secured to the post. A healing period for the implant typically lasts three to six months, during which a patient's gums heal, and osseo-integration occurs.

Osseo-integration is a process in which bone is apposed to a surface of the implant. After the healing period, the dentist surgically cuts into soft tissue to expose a coronal surface of the post, to which a permanent abutment, including a replacement tooth, is secured in place of the original prosthetic abutment. An alternative procedure does not submerge the implant for a healing period, but instead uses a permanent abutment instead of a temporary prosthetic abutment at a time of implant placement into a jaw bone. In such an alternative procedure, the implant post and the abutment may be one solid structure.

Mucoperiosteum: a type of oral mucosa which has a fibrous lamina propria, no submucosa (loose connective tissue), and is attached to the underlying periosteum of bone. The attached gingiva is a keratinized mucoperiosteum, a firm tissue.

Implant Abutment Function and Design

The dental implant abutment, which usually consists of one solid piece, fulfills three functions: (1) the abutment secures a precise engagement between the prosthetic element (external) of the implant and the coronal surface of implant post (internal); (2) the abutment adheres to the upward emerging contour profile of the marginal gingiva including papilla; (3) the abutment interfaces with a prosthetic device such as a crown.

For purposes of better understanding some embodiments of the present invention, reference is now made to FIG. 1A, which is an image of a complete dental implant according to prior art.

FIG. 1A depicts an image of a complete dental implant, including a post 101 for implanting in bone; a crown 103, which is a tooth prosthesis; and an abutment section 102, serving for connecting the crown 103 to the post 101.

Reference is now made to FIG. 1B, which is an image of a problem which occurs with some dental implants according to prior art.

FIG. 1B depicts dental implants, including crowns 111, and problems with receding gums 113, receding even as much as exposing the posts, which occasionally occur when prior art dental implants are used.

Reference is now made to FIG. 1C, which is an image comparing a gum tissue problem which occurs with some dental implants according to prior art, and healthy gum tissue.

FIG. 1C depicts papilla of gingiva 115 which does not fill an interdental space, probably because periosteum is pulling the gingiva up, and normal papilla 116 which does fill the interdental space.

Reference is now made to FIG. 1D, which is an image of a prior art post 121, without an abutment (not shown) and crown (not shown).

Reference is now made to FIG. 1E, which is an image of a prior art single piece dental implant 131, including a post 132 and an abutment 133.

Additional background art includes:

An article by Dwek J R, titled: "The periosteum: what is it, where is it, and what mimics it in its absence?" published in Skeletal Radiol, (2010), 39(4): 319-23.

An article by Consolaro A and Furquim L., titled" "Intrusive mechanics generates inclination forces and orthopedic stimulus followed by simultaneous dental repositioning and bone remodeling", published in Dental Press J Orthod. 2011 September-October; 16(5):20-9.

An article by Knothe Tate M L, Chang H, Moore S R and Knothe U R, titled: "Surgical Membranes as Directional Delivery Devices to Generate Tissue: Testing in an Ovine Critical Sized Defect Model", published in PLoS ONE (2011) 6(12): e28702. doi:10.1371/journal.pone.0028702.

PCT Published Patent Application No. WO 2008/004220 of Binderman et al, for "DEVICE AND METHOD FOR GINGIVAL ATTACHMENT ASSOCIATED WITH ENDOSSEOUS IMPLANTS".

The disclosures of all references mentioned above and throughout the present specification, as well as the disclosures of all references mentioned in those references, are hereby incorporated herein by reference.

SUMMARY OF THE INVENTION

The present invention, in some embodiments thereof, includes a design of a radial extension to a dental implant, and a method of treating gums at an implant site such that growth of the periosteum is guided onto an extended base of the abutment, or an extended coronal base of the implant post, enabling its attachment and facilitates its desired emerging profile. Gingiva potentially follows the periosteum path and as a result a better gingival profile is achieved relative to current practice.

The term "dental implant" in all its grammatical forms is used throughout the present specification and claims to mean both a single piece dental implant, which for example, includes an implant and an abutment in one piece such as depicted in FIG. 1E, and a multi-piece dental implant, which, for example, has a separate implant and abutment, such as depicted in FIGS. 1A and 1D, and potentially even more pieces.

The term "post" in all its grammatical forms is used throughout the present specification and claims to mean a section of a dental implant which is sunk into bone.

The term "abutment" in all its grammatical forms is used throughout the present specification and claims to mean a section of a dental implant which connects a crown to a post, including an abutment in one piece with a post, an abutment in one piece between a post and a crown, and even a two-piece, or multi-piece, abutment, as depicted as optional abutment configurations, by way of some non-limiting example, in FIGS. 4, 5 and 6.

According to an aspect of some embodiments of the present invention there is provided a dental implant including a subperiosteal extension, the extension extending radially beyond a radius of a post of the dental implant.

According to some embodiments of the invention, the subperiosteal extension is included in an abutment portion of the dental implant.

According to some embodiments of the invention, the dental implant is a single piece dental implant including both a post and an abutment in a single piece.

According to some embodiments of the invention, the subperiosteal extension extends radially between 0.5 to 3 millimeters from a circumference of a post of the dental implant.

According to some embodiments of the invention, an outer circumference of the subperiosteal extension is asymmetric with reference to a center axis of the dental implant.

According to some embodiments of the invention, the subperiosteal extension includes perforations. According to some embodiments of the invention, the subperiosteal extension includes perforations allowing flow of cells therethrough. According to some embodiments of the invention, the subperiosteal extension includes perforations no larger than 50 micrometer in diameter.

According to some embodiments of the invention, the dental implant is coated on a surface facing periosteum with at least one material selected from a group consisting of gold, silicium, and a polymer for attaching and anchoring periosteum.

According to an aspect of some embodiments of the present invention there is provided a device for mounting onto a dental implant configured to extend the dental implant to include a subperiosteal extension, the device extending radially beyond an interface between bone and the dental implant.

According to some embodiments of the invention, the device is configured to mount on the dental implant surrounding an abutment portion of the dental implant.

According to some embodiments of the invention, the device is configured to serve as an abutment base, being configured to mount on an implant post of the dental implant and to have mounted thereon an additional portion of an abutment of the dental implant.

According to some embodiments of the invention, the device includes perforations.

According to an aspect of some embodiments of the present invention there is provided a method of implanting a dental implant including elevating a mucoperiosteal flap at site of implantation, drilling a hole for inserting a dental implant including a subperiosteal extension, inserting the dental implant, and covering the subperiosteal extension with the mucoperiosteal flap.

According to some embodiments of the invention, the drilling includes drilling with a drill which produces a recess in bone crest configured to accept the subperiosteal extension, and the inserting the dental implant includes locating the subperiosteal extension in the recess.

According to some embodiments of the invention, producing a recess in bone crest configured to accept the subperiosteal extension includes producing a recess having an asymmetric outer circumference with reference to a center axis of the hole produced by the drilling a hole.

According to some embodiments of the invention, the recess is produced into bone crest to a depth equal to or greater than a thickness of the subperiosteal extension.

According to some embodiments of the invention, locating the subperiosteal extension includes locating the subperiosteal extension such that a bottom of the subperiosteal extension is snug against bone at a bottom of the recess.

According to some embodiments of the invention, locating the subperiosteal extension includes locating the subperiosteal extension such that a top of the subperiosteal extension is at a level of bone level adjacent to the recess.

According to some embodiments of the invention, locating the subperiosteal extension includes locating the subperiosteal extension such that a top of the subperiosteal extension is below a level of bone level adjacent to the recess.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings.

DESCRIPTION OF SPECIFIC EMBODIMENTS OF THE INVENTION

Figure 1A:
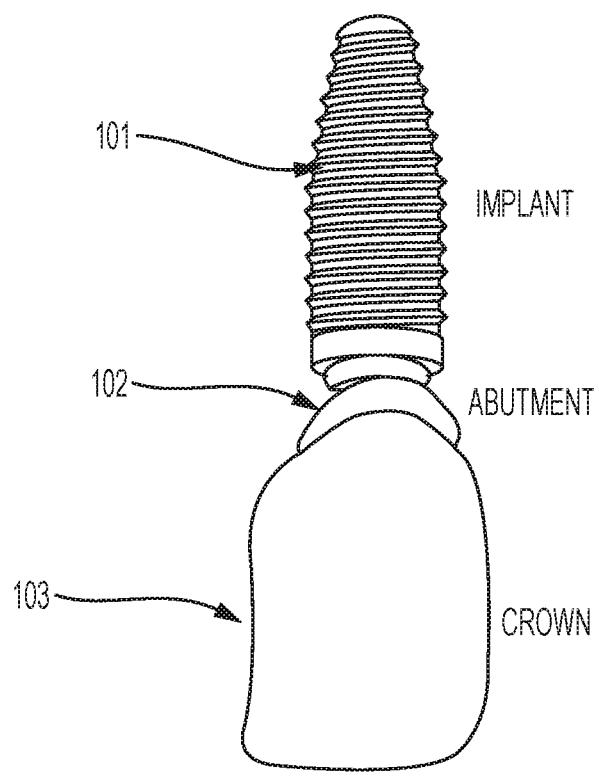
FIG. 1A is an image of a complete dental implant according to prior art.
Figure 1B:
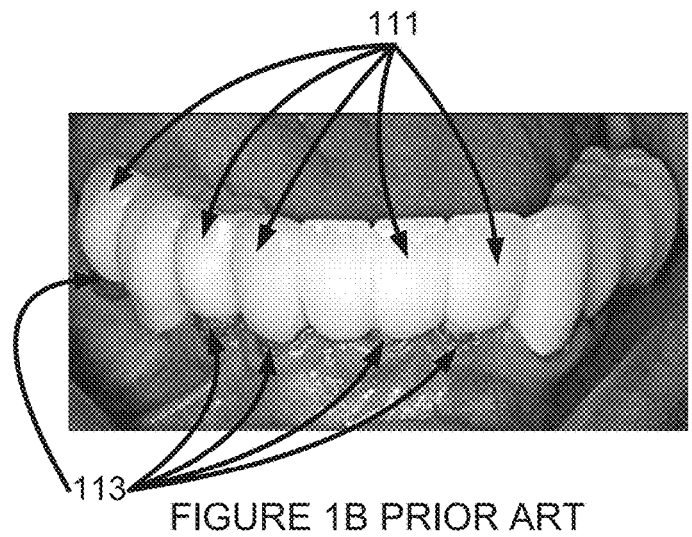
FIG. 1B is an image of a problem which occurs with some dental implants according to prior art.
Figure 1C:
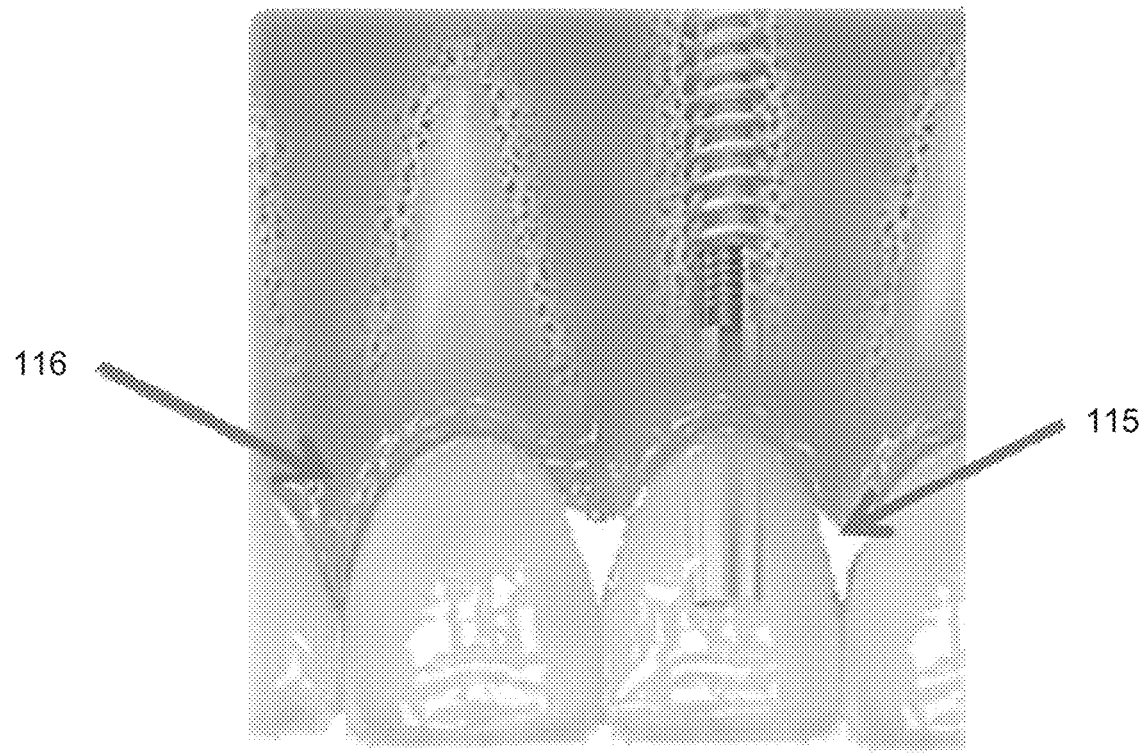
FIG. 1C is an image comparing a gum tissue problem which occurs with some dental implants according to prior art, and healthy gum tissue.
Figure 1D:
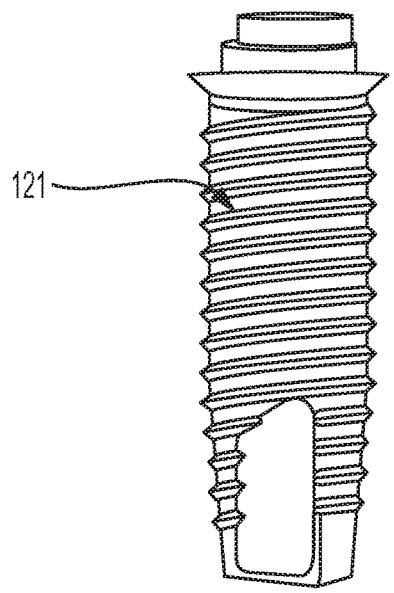
FIG. 1D is an image of a prior art post, without an abutment and crown.
Figure 1E:
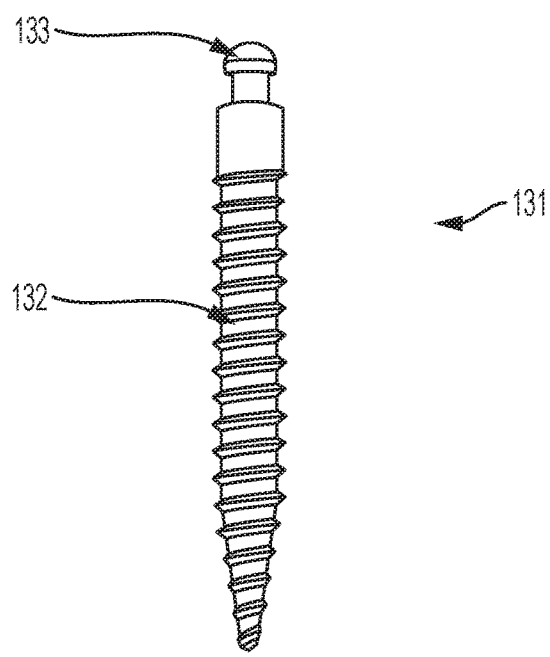
FIG. 1E is an image of a prior art single piece dental implant, including a post and an abutment.

The present invention, in some embodiments thereof, relates to a dental implant and, more particularly, but not exclusively, to a dental implant with an extended sub-periosteal base and to a sub-periosteal base extension for a dental implant.

A challenge today is to achieve a marginal gingiva profile, especially of interdental papilla, which can restore a normal esthetic profile of the gums. The marginal gingiva is a terminal edge of gingiva surrounding teeth in a collar-like fashion. The marginal gingiva is supported and stabilized by collagen fibers (Sharpey fibers) which attach the gingiva to tooth root surface above the periosteum bone level and below the tooth crown.

Prior art abutments are typically designed to have a vertical emerging profile, resembling a ramp, narrower in diameter than a crown part of abutment, to which a base of an abutment is secured, with an intention of allowing the gingiva to grow over a periphery of the coronal surface of the implant post towards the abutment, with an intent to produce a natural looking gingival profile.

Despite such abutments, a normal gingival profile surrounding the artificial crown is often not achieved. The inventors have discovered that the normal gingival profile surrounding the artificial crown is not achieved probably because the marginal gingiva is guided by the periosteum lining the bone.

An aspect of some embodiments of the invention has to do with providing a component of a dental implant which extends over the crevice or gap in bone where an implant post is implanted, and preferably prevents periosteum from growing into the gap or crevice.

An aspect of some embodiments of the invention has to do with providing a component of a dental implant which extends over the gap or crevice in bone where an implant post is implanted, and preferably guides periosteum onto the extension.

In some embodiments a recess is produced in bone around an implant post, so that the extension fits into the recess. The recess is optionally sized so that the bottom of the extension is snug against bone crest, optionally preventing the periosteum to grow along the bone and into the implant post crevice or gap.

In some embodiments the recess is optionally sized so that the top of the extension is level with bone crest, potentially guiding the periosteum to grow along the extension and into the implant post crevice or gap.

In aspects of the invention, the extension may optionally be part of an implant abutment, or a separate component added to the dental implant, or part of a one-piece or of a two-piece implant abutment.

In aspects of the invention, the extension, or at a surface of the extension facing periosteum may optionally be coated with a material which has an ability to allow attachment and anchoring of periosteum cells.

In aspects of the invention, the extension optionally includes perforations through the extension.

The present invention, in some embodiments thereof, includes a design of a radial extension to a dental implant, and a method of treating gums at an implant site such that growth of the periosteum is guided onto a base of the abutment, or the extension of the implant, enabling its attachment and facilitates its desired emerging profile.

The present invention, in some embodiments thereof, relates to dental implants which are designed to provide periosteum and gingiva with direct physical and biological surface attachment potentially resulting in significant aesthetic and functional benefits to the patient.

The present invention, in some embodiments thereof, relates to a design of a radial extension to the dental implant located approximately at a base of an abutment secured to a coronal surface of an implant post, and extending beyond the implant post perimeter.

In some embodiments an extension part is placed directly on the jaw bone crest, therefore guiding the direction of growth of periosteum and gingival tissue over the extension.

In some embodiments the periosteum, which covers the extension, attaches to specific areas on the extension, by chemical biological interaction as described in above-mentioned PCT Published Patent Application No. WO 2008/004220.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

A Dental Implant with an Extended Sub Periosteal Base

Figure 2A:
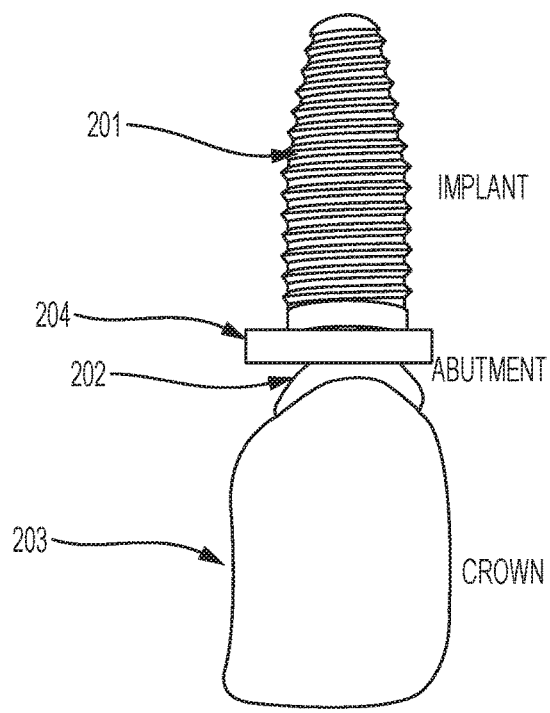
FIG. 2A is a simplified illustration of a dental implant with an extended sub-periosteal base according to an example embodiment of the invention.

Reference is now made to FIG. 2A, which is a simplified illustration of a dental implant with an extended sub-periosteal base according to an example embodiment of the invention.

FIG. 2A depicts a dental implant, including a post 201 for implanting in bone; a crown 203, which is a tooth prosthesis; and an abutment 202, serving for connecting the crown 203 to the post 201.

FIG. 2A depicts an extension 204, between the abutment 202 and the post 201. The extension 204 extends the dental implant radially approximately at a location where the dental implant exits the bone in which the post is implanted.

In various embodiments the extension 204 is part of the post 201; part of the abutment 202; or an additional part added onto the dental implant approximately at the location depicted in FIG. 2A.

An Extended Sub Periosteal Base as an Addition to a Dental Implant

Figure 2B:
FIGS. 2B and 2C are simplified side view and top view illustrations of an extension for adding onto a dental implant according to an example embodiment of the invention.
Figure 2C:
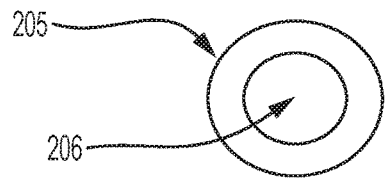

Reference is now made to FIGS. 2B and 2C, which are simplified side view and top view illustrations of an extension 205 for adding onto a dental implant according to an example embodiment of the invention.

FIGS. 2B and 2C depict a side view and a top view respectively of a ring-shaped extension 205, having a hole 206, for adding as a sub-periosteal extension, through the hole 206, onto a dental implant according to an example embodiment of the invention.

Figure 2D:
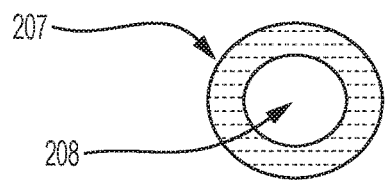
FIG. 2D is a simplified top view illustration of an extension for adding onto a dental implant according to an example embodiment of the invention.

An Example Embodiment in which the Sub Periosteal Extension Includes Perforations Reference is now made to FIG. 2D, which is a simplified top view illustrations of an extension 207 for adding onto a dental implant according to an example embodiment of the invention.

FIG. 2D depicts a top view of a ring-shaped extension 207, having a hole 208, for adding as a sub-periosteal extension, through the hole 208, onto a dental implant according to an example embodiment of the invention. The extension 207 in the embodiment of FIG. 2D includes perforations through the extension 207.

In some embodiments, the perforations are no larger than 50 micrometer in diameter.

It is noted that the above description of perforations applies as well to an extension which is part of an implant and/or an abutment (by way of a non-limiting example such as depicted in FIGS. 2A (204), 2E (212), 2F (216), 2G (221), 4 (23), 5 (623), 6 (723a) and 7 (807)), and not only to separate extensions (by way of a non-limiting example such as depicted in FIGS. 2B (205), 2C (205) and 2D (207)).

The Sub Periosteal Extension Extends Beyond a Radius of the Implant Section

In some embodiments the extension 204 205 207 extends beyond a radius of the post, designed to at least cover a gap between the post and a bone in which the post is implanted.

In some embodiments, the extension 204 205 207 extends radially between 0.5 to 3 millimeters out from a circumference of the post, or in other words, 0.5 to 3 millimeters beyond a radius of the post.

The Sub Periosteal Extension May be a Portion of Various Components of a Dental Implant FIGS. 2B, 2C and 2D depict ring-shaped extensions having a hole, for adding as a sub-periosteal extension onto a dental implant. In some embodiments of the invention, the sub-periosteal extension may be a portion of various components of a dental implant.

Figure 2E:
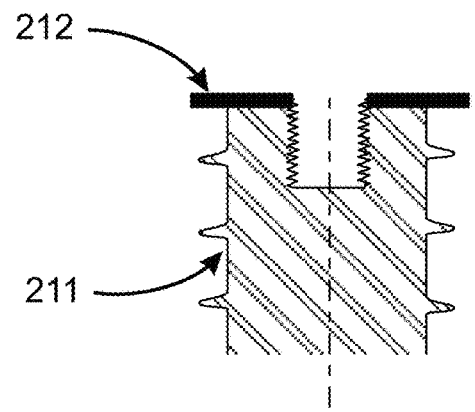
FIG. 2E is a simplified illustration of a side view cross section of an example embodiment of the invention.

Reference is now made to FIG. 2E, which is a simplified illustration of a dental implant post 211 which includes a sub-periosteal extension 212 according to an example embodiment of the invention.

Figure 2F:
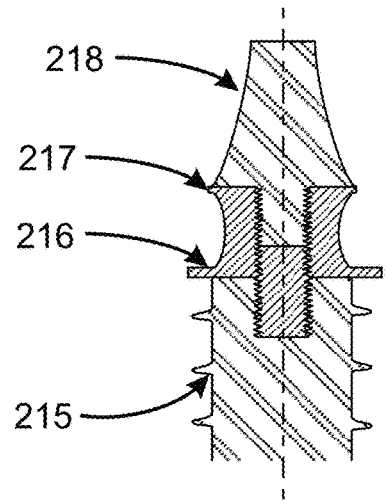
FIG. 2F is a simplified illustration of a side view cross section of an example embodiment of the invention.

Reference is now made to FIG. 2F, which is a simplified illustration of a dental implant post 215, into which an abutment base 217 has been inserted. The abutment base 217 includes s sub-periosteal extension 216. An optional additional abutment component 218 is depicted as inserted into the abutment base 217.

Figure 2G:
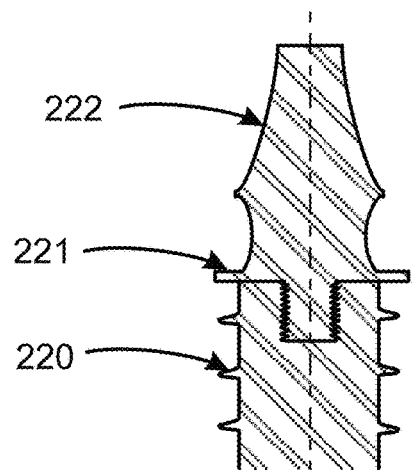
FIG. 2G is a simplified illustration of a side view cross section of an example embodiment of the invention.

Reference is now made to FIG. 2G, which is a simplified illustration of a dental implant post 220, into which an abutment 221 has been inserted. The abutment base 221 includes s sub-periosteal extension 221.

The Thickness of Example Embodiments of the Sub Periosteal Extension

In some embodiments, the thickness of the extensions 204 205 207 212 216 221 is thin enough such that the extensions 204 205 207 212 216 221 are flexible.

In some embodiments, the thickness of the extensions 204 205 207 212 216 221 is in a range between 0.2 mm and 2 mm.

In some embodiments, a recess is made into bone crest and the extensions 204 205 207 212 216 221 sit in the recess. In some embodiments the extensions 204 205 207 212 216 221 are as thick as the depth of the recess, in some embodiments less than the depth of the recess. Conversely, in some embodiments the recess is produced to be as deep as a thickness of the extensions 204 205 207 212 216 221, and in some embodiments the recess is produced to be deeper than the thickness of the extensions 204 205 207 212 216 221.

In some embodiments, it is the implant post which is inserted into bone such that its coronal surface is at, or very near to, a level of the bottom of the recess.

Example Materials of which the Sub Periosteal Extension May be Made of

In some embodiments, the extension 204 205 207 212 216 221 is made of one or more materials selected from a group consisting of: titanium; a titanium alloy; gold; zirconium; a biocompatible polymer; and a biocompatible solid material.

Example Materials with which the Sub Periosteal Extension May be Coated

In some embodiments, the surface of the extensions 204 205 207 212 216 221 is coated with at least one material selected from a group consisting of: gold; silicium; and a polymer which has an ability to allow attachment and anchoring of periosteum cells.

In some embodiments, at least the surface facing periosteum of the extensions 204 205 207 212 216 221 is coated with at least one material selected from a group consisting of: gold; silicium; and a polymer which has an ability to allow attachment and anchoring of periosteum cells.

Optional Preparing of Bone for Accepting the Extension

In some embodiments, a patient's bone is prepared to accept the sub-periosteal extension.

In some embodiments, bone is flattened surrounding a location of the implant, at least at a radius sufficient to include the extensions 204 205 207 212 216 221.

In some embodiments, a recess is produced in bone surrounding a location of the implant, at least at a radius sufficient to include the extensions 204 205 207 212 216 221.

In some embodiments, the recess is produced in bone surrounding a location of the implant, is produced to have a radius equal to a radius of the extensions 204 205 207 212 216 221.

In some embodiments, the recess is produced in bone surrounding a location of the implant, is produced to have a radius larger than the radius of the extensions 204 205 207 212 216 221.

In some embodiments the depth of the recess is more than a thickness of the extensions 204 205 207 212 216 221.

In some embodiments the depth of the recess is equal to a thickness of the extensions 204 205 207 212 216 221.

In some embodiments a bottom of the extensions 204 205 207 212 216 221 is located snug against bone at a bottom of the recess.

In some embodiments the depth of the recess is between 0.5 mm and 2 mm.

Figure 3:
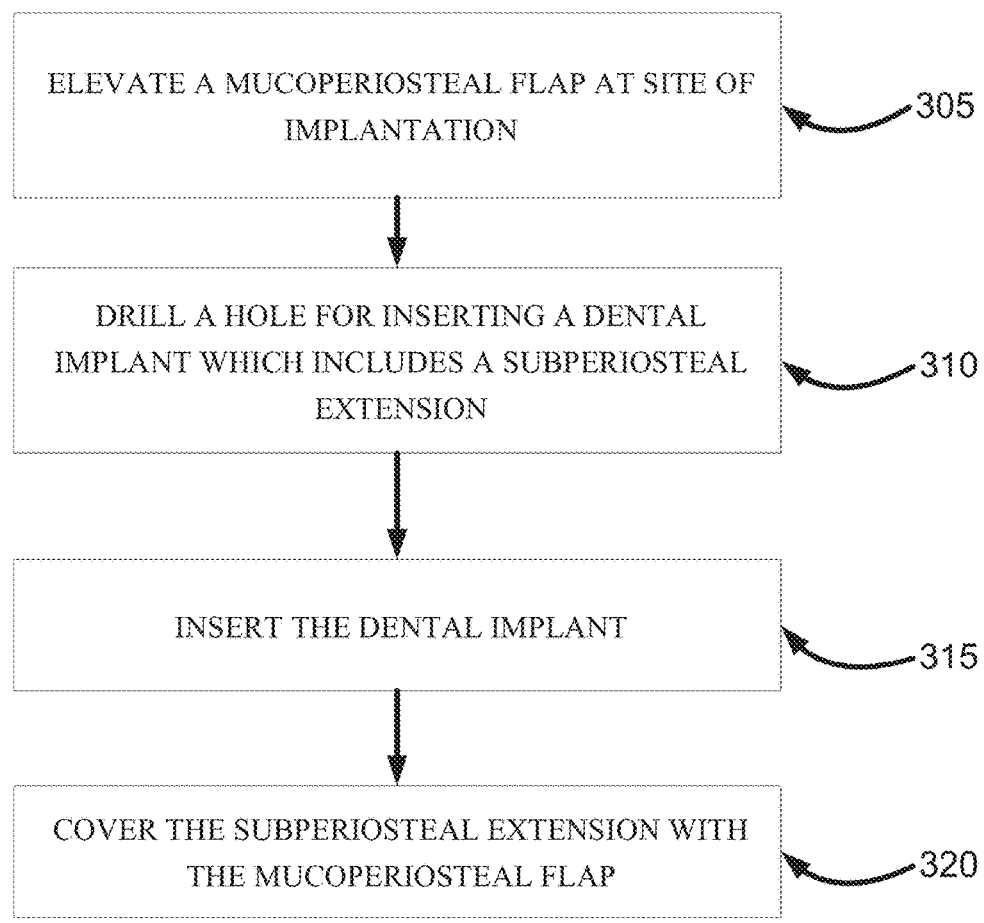
FIG. 3 is a simplified flow chart illustration of a method of implanting a dental implant according to an example embodiment of the invention.

An Example Embodiment of a Method for Implanting a Dental Implant which Includes a Subperiosteal Extension Reference is now made to FIG. 3, which is a simplified flow chart illustration of a method of implanting a dental implant according to an example embodiment of the invention.

The method depicted by FIG. 3 includes:

elevating a mucoperiosteal flap at site of implantation (305);

drilling a hole for inserting a dental implant which includes a subperiosteal extension (310);

inserting the dental implant (315), optionally below the crest, optionally level with the recess height; and covering said subperiosteal extension with said mucoperiosteal flap (320).

In some embodiments, the inserting the dental implant includes inserting a post, and also locating a subperiosteal extension onto the post.

In some embodiments, the inserting the dental implant (315) includes attaching or fixing the subperiosteal extension to the implant post firmly.

In some embodiments, the drilling includes drilling with a drill which produces a recess in bone crest configured to accept the subperiosteal extension, and the inserting the dental implant mounting the subperiosteal extension includes locating the subperiosteal extension such that the subperiosteal extension is located in the recess.

In some embodiments, the producing a recess in bone crest configured to accept a subperiosteal extension includes producing a recess having an asymmetric outer circumference with reference to a center axis of a hole produced by the drilling a hole.

In some embodiments, the recess is produced to be between 0.1 mm and 1.0 mm deep into bone crest.

In some embodiments, the recess is produced into bone crest to a depth equal to a thickness of the subperiosteal extension. In some embodiments, the recess is produced into bone crest to a depth greater than a thickness of the subperiosteal extension.

In some embodiments, the mounting of the subperiosteal extension includes mounting the subperiosteal extension such that a bottom of the subperiosteal extension is snug against bone at a bottom of the recess.

In some embodiments, the mounting of the subperiosteal extension includes mounting the subperiosteal extension such that a top of the subperiosteal extension is at a level of bone level adjacent to the recess.

In some embodiments, the mounting of the subperiosteal extension includes mounting the subperiosteal extension such that a top of the subperiosteal extension is below a level of bone level adjacent to the recess.

In some embodiments, the method further includes suturing the mucoperiosteal flap over the subperiosteal extension.

It is noted that the description of the above mentioned method applies to all forms of a dental implant which includes a subperiosteal extension, whether the subperiosteal extension is part of an implant or part of an abutment (by way of a non-limiting example such as depicted in FIGS. 2A, 4, 5 and 6), or a separate part added to a dental implant with no subperiosteal extension (by way of a non-limiting example such as depicted in FIGS. 2B, 2C and 2D).

Additional Description of Embodiments

Figure 4:
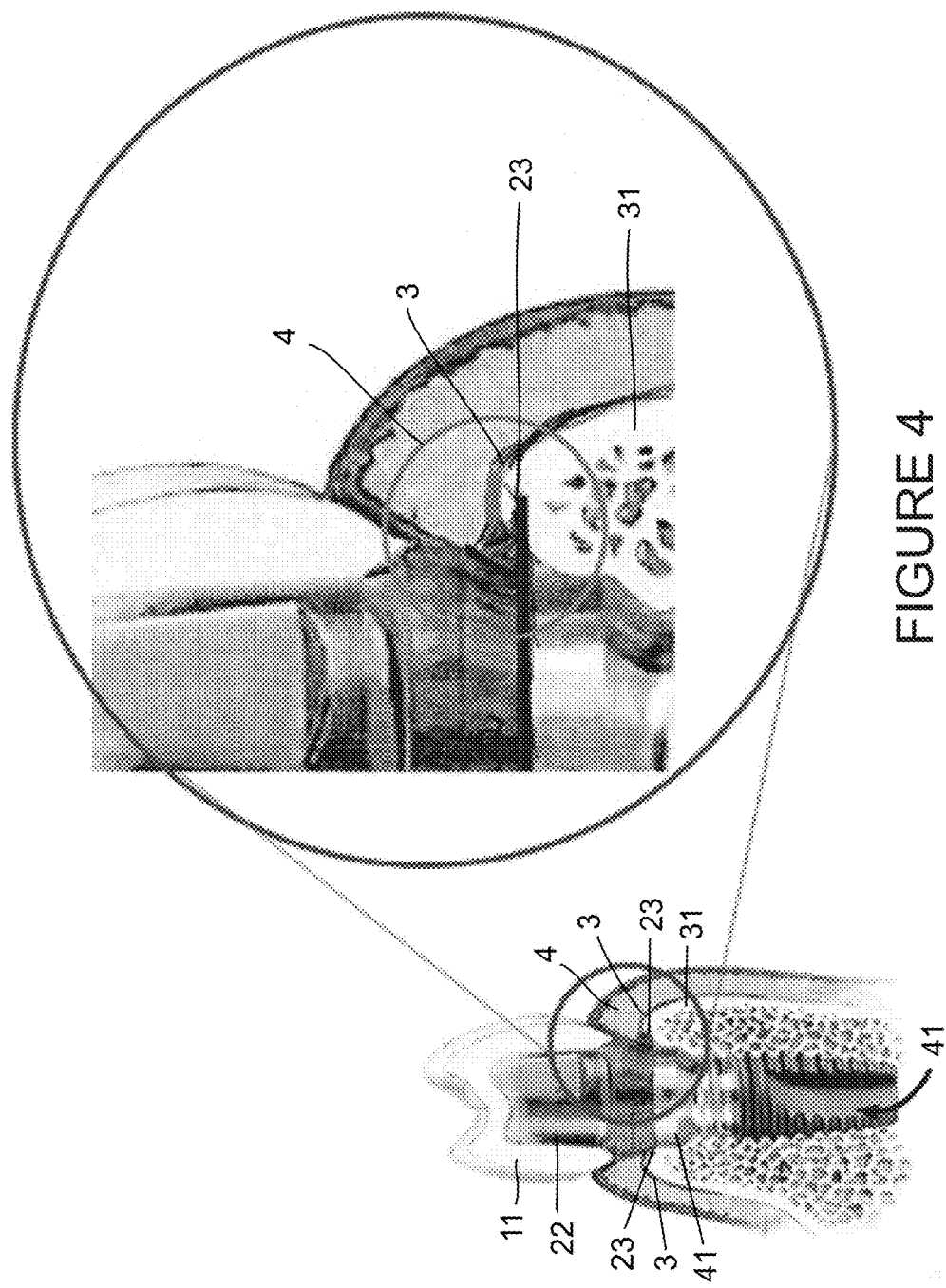
FIG. 4 is a simplified illustration of a side view cross section of an example embodiment of the invention.

Reference is now made to FIG. 4, which is a simplified illustration of a side view cross section of an example embodiment of the invention.

FIG. 4 depicts a cross sectional side view of a jawbone crest 31, into which a post 41 has been inserted. FIG. 4 also depicts an abutment 22 attached to the post 41 and a prosthetic crown 11 attached to the abutment 22.

FIG. 4 depicts an extension 23 of the abutment 22 onto the jawbone crest 31, and periosteum 3 gingiva 4 sutured and/or growing over the extension 23.

In some embodiments, design of the abutment 22 includes an extension 23, which may be termed a seating base, which is mounted to a coronal surface of a post and extends at least 1 mm beyond the post's external periphery onto a crest of a jaw bone surface. The extension 23 acts as a continuous surface for periosteum 3 growth onto the base of the abutment 22. In some embodiments, the periosteum and the gingival, which optionally cover the abutment 22 base surface at least 1.5 mm, is also opposed to the vertical emerging profile of the abutment 22, allowing periosteum and gingiva cells to attach to the vertical profile of the abutment 22 as well.

In some embodiments, the surface of the abutment 22 which is facing the periosteum and/or the vertical emerging profile of the abutment 22 are optionally coated with compounds which biologically attach cells to titanium as described in published PCT Patent Application No. WO 2006/21085 and in U.S. Provisional Patent Application No. 61/277,423.

Figure 5:
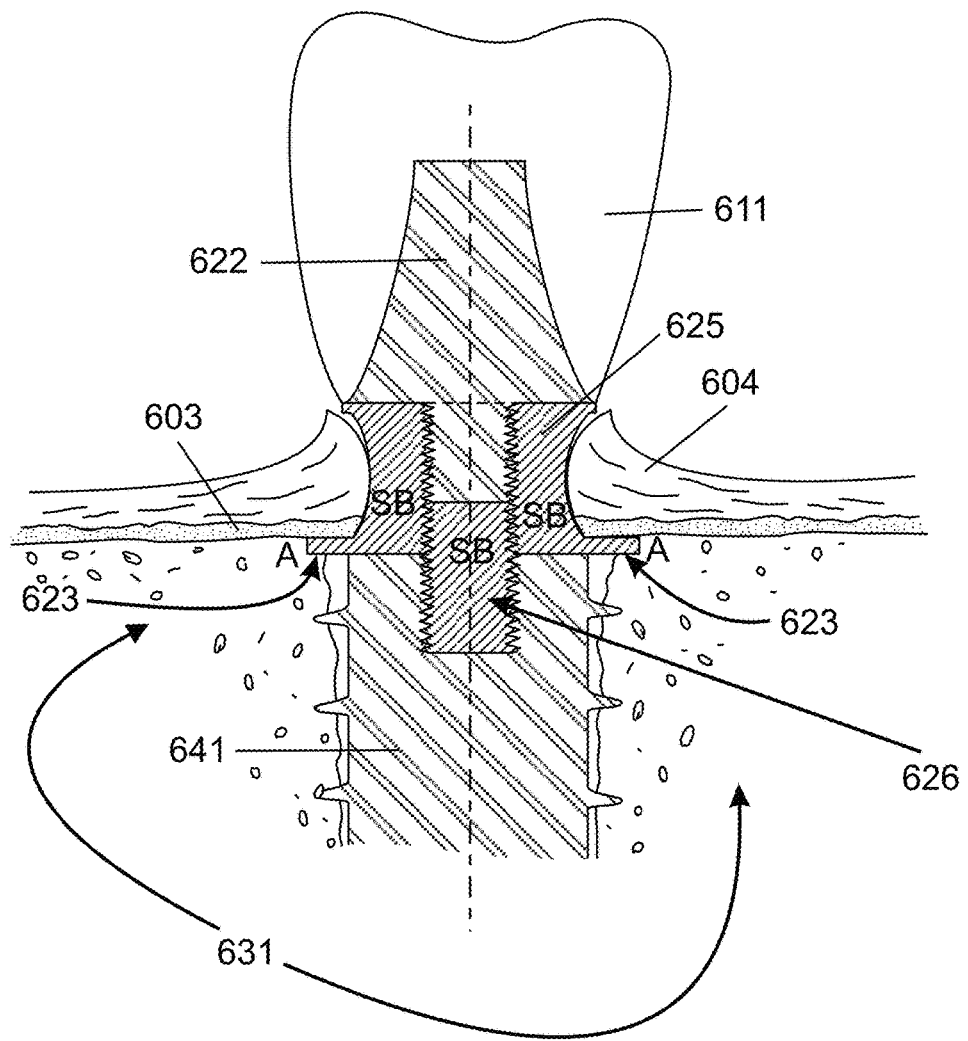
FIG. 5 is a simplified illustration of a side view cross section of an example embodiment of the invention.

Reference is now made to FIG. 5, which is a simplified illustration of a side view cross section of an example embodiment of the invention.

FIG. 5 depicts a cross sectional side view of a jawbone crest 631, into which a post 641 has been inserted. FIG. 5 also depicts an abutment 622 attached to an abutment base 625, which is attached to the post 641, and a prosthetic crown 611 attached to the abutment 622.

FIG. 5 depicts the abutment base 625 having an extension 623 of the abutment base 625 onto the jawbone crest 631, and periosteum 603 and gingiva 604 sutured and/or growing over the extension 623 and the abutment base 625.

In some embodiments the abutment base 625 includes two parts—an abutment base 625 and a screw 626 for attaching the abutment base 625 to the post 641.

In some embodiments the abutment base 625 is constructed as one part which includes the screw 626 for attaching the abutment base 625 to the post 641.

Figure 6:
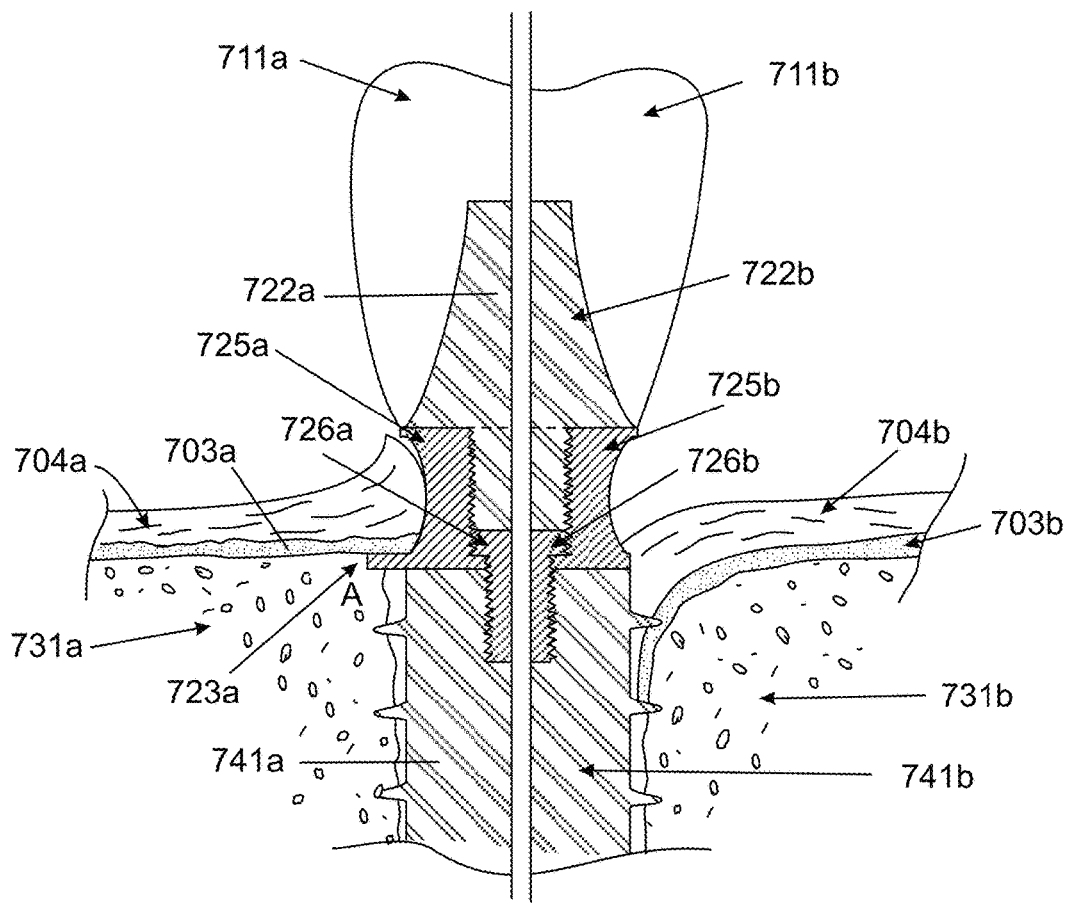
FIG. 6 is a simplified illustration of a side view cross section of an example embodiment of the invention compared to a side view cross section of a prior art dental implant exhibiting receding gums.

Reference is now made to FIG. 6, which is a simplified illustration of a side view cross section of an example embodiment of the invention compared to a side view cross section of dental implant exhibiting receding gums.

FIG. 6 depicts a cross sectional side view of jawbone crests 731a 731b, into which posts 741a 741b have been inserted. FIG. 6 also depicts abutments 722a 722b attached to abutment bases 725a 725b, which are attached to the posts 741a 741b, and prosthetic crowns 711a 711b attached to the abutments 722a 722b.

FIG. 6 depicts the abutment base 725a having an extension 723a of the abutment base 725a onto the jawbone crest 731a, and periosteum 703a and gingiva 704a sutured and/or growing over the extension 723a and the abutment base 725a.

In contrast, FIG. 6 also depicts the abutment base 725b NOT having an extension of the abutment base 725b, and periosteum 703b and gingiva 704b growing into a space between the jawbone crest 731b and the post 741b.

Figure 7:
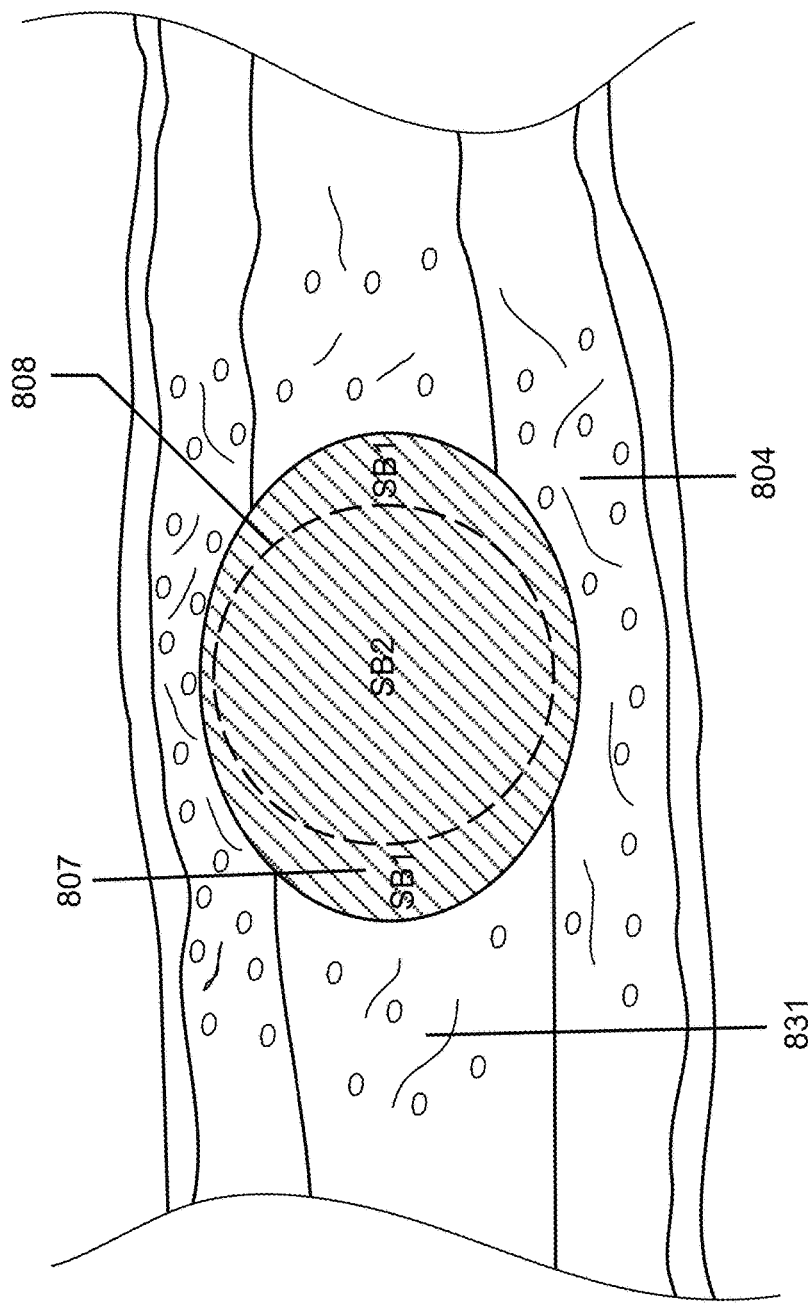
FIG. 7 is a simplified illustration of a top view cross section of an example embodiment of the invention.

Reference is now made to FIG. 7, which is a simplified illustration of a top view cross section of an example embodiment of the invention.

FIG. 7 depicts a cross-sectional top view of a jawbone crest 831, into which a post (not shown) has been implanted, and cortical bone plates, buccal and lingual 804 surround the jawbone crest 831. Between the cortical bone plates, the bone is cancellous (trabecular bone). The cancellous bone 831 which is located in between implants allows ingrowth of periosteum (periosteum growth only on mineralized and solid surfaces). Therefore, support by an extension surface is optionally used to guide periosteum growth, supporting the gingiva papilla. Trabecular bone consists of gaps with soft tissue. FIG. 7 also depicts an abutment extension 807, and optionally a central hole 808 through the abutment extension 807.

A Possible Biological Explanation

Periosteum tissue includes osteogenic cells and tissue which adheres to the mineralized matrix surfaces, like the buccal and lingual plates, and is capable of producing new bone. Lateral of bone surface, the periosteum is made of soft connective tissue which supports the mucose epithelial tissue (gum tissue). Both the periosteum and the connective tissue are also termed mucoperiosteal tissue. Being part of the bone, the periosteum lining typically follows the shape of the bone surface. In natural dentition, Sharpey fibers (collagen fibers) extending from the root surface are mingled into periosteum tissue that covers the crest of the jaw bone. From the periosteum of crestal bone fibrous tissue extends into marginal gingiva including papillae. Thus periosteum is part of the bone as well as part of gingiva. Periosteum and gingiva are termed mucoperiosteum.

In some embodiments, and referring again to FIG. 4, a design for an extension 23 to an abutment 22 is provided, which is optionally secured to the coronal aspect of the post 41 such that the extension 23 covers the coronal implant surface and extends at least 1.0 mm beyond an external periphery of the post 41.

In some embodiments the thickness of the extension 23 is between 0.5 mm and 1 mm, and the extension 23 is positioned on the bone crest 31 below the periosteum 3.

In some embodiments, a vertical emerging profile aspect of the abutment 22 is 1 mm to 2.5 mm narrower than an external periphery of the implant post 41. In such embodiments the periosteum including the gingiva can potentially cover the horizontal periphery until the periosteum and the gingiva meet the vertical emerging profile.

In some embodiments, the surface of the abutment 22 which is to be covered by the periosteum 3 is coated to create a biological attachment of the periosteum, as described in published PCT Patent Application No. WO 2006/21085 and in U.S. Provisional Patent Application No. 61/277,423.

In some embodiments, the surface of the vertical emerging aspect of the abutment 22 which faces the gingival cells and tissue is coated similarly, to potentially biologically bond the cells to this profile.

In some embodiments, the extension 23 part and the vertical emerging profile of the abutment 22 are formed as one piece, while the prosthetic part of the abutment is an additional part fixed to the emergence profile and to the post 41.

In some embodiments, the extension 23 is believed to prevent the resorption of peri-implant bone.

In some embodiments the abutment 22 includes an extension 23 and attachable surface, the extension 23 having a first surface that is complementary to a coronal surface of a coronal part of the dental implant. The extension 23 surface of the abutment 22 extends the periphery of the coronal part of the implant, allowing the periosteum 3 to cover and biologically bind to this part of abutment 22.

In the example embodiment depicted in FIG. 4, the extension 23 of the abutment 22 closely embraces a peripheral surface of the implant and is situated below the level of periosteum 3 in the bone 31.

From this extended periphery the abutment converges vertically, producing a depression allowing marginal gingiva to engage and attach to a surface of the abutment extension 23. A gingival part of the abutment profile is approximately 2-5 mm interproximally, 2-3 mm lingually and 0-2 mm bucally, similar to a natural pattern of marginal gingiva. A prosthetic part of abutment extends from the extension part, enabling attachment of a crown (see reference 625 in FIG. 5).

Yet Another Description of Embodiments

In some embodiments of the invention, the following method is used for surgically placing a dental implant constructed according to an example embodiment of the invention:

A. Elevating a mucoperiosteal flap at a site of implantation.

B. Indicating a point of implant insertion by a round small burr.

C. Drilling from 2 mm diameter to a diameter one drill size short of a drill needed for inserting a post.

D. Drilling with a drill which prepares a sink, or recess, in bone crest, which is shaped to accept the extension. The recess preferably extends further than a gap between bone and post interface. The depth of the recess is preferably such that the depth corresponds to a height of the subperiosteal extension base, or in some embodiments even deeper, for example between 0.1-1.0 mm. The recess in the bone crest potentially produces a seat for the subperiosteal base (extension) of the abutment.

D1. In some embodiments the preparation of the recess in the bone is optionally prepared by tools capable of producing an asymmetric shape. In some embodiments such tools are prepared for specific subperiosteal base geometries, optionally when implants are inserted in extraction sites, or after peri-implantitis surgery. In some embodiments, non-rotational bone cutting instruments, such as, by way of a non-limiting example, Piezo-surgical instruments, can reduce and shape bone to any kind of symmetric or asymmetric shape.

E. Inserting and securing the subperiosteal base of the abutment (the extension) to the implant post with a screw or other fastening. A top of a subperiosteal base extension preferably sits at a level, or minimally below the level, of a neighbor bone level, to allow overgrowth of periosteum. In some embodiments the implant post is placed such that its coronal surface is level with a bottom of a recess for placing the subperiosteal extension.

F. Adapting and suturing the mucoperiosteal flap over the abutment extension.

In some embodiments of the invention, the following method is used for surgically adding an extension to an existing dental implant, even a prior art existing dental implant, according to an example embodiment of the invention:

A. In some scenarios, such as, by way of a non-limiting example, in cases of peri-implantitis, surgery exposing the implant is performed.

B. Granulation tissue, if any is found, is removed, and the implant is optionally cleaned by a cleansing solution.

C. A ring-shaped extension surrounding the implant and extending from a perimeter of the implant is inserted to bridge a gap between implant and bone.

D. A mucoperiosteal flap is optionally formed, leaving a coronal part of the implant exposed, and the mucoperiosteal flap is optionally sutured over the extension, and adapted to the implant.

It is expected that during the life of a patent maturing from this application many relevant materials for a dental implant will be developed, and the scope of the invention is intended to include all such new technologies a priori.

It is expected that during the life of a patent maturing from this application many relevant materials for enabling periosteum to adhere thereto will be developed, and the scope of the invention is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of preventing periosteum and gingiva from growing into a space between a jawbone crest and a dental implant, the method comprising:
    elevating a mucoperiosteal flap, including periosteum and gingiva, at site of implantation;
    drilling a hole in bone for inserting a dental implant comprising a subperiosteal extension and a post, the subperiosteal extension covering an entire top surface of the post, the subperiosteal extension being configured to accommodate a prosthesis, and the subperiosteally extension extending radially beyond a radius of the post of said dental implant;
    inserting said dental implant; and
    covering said subperiosteal extension with said mucoperiosteal flap, including said periosteum, such that said periosteum and gingiva to grow on said sub-periosteal extension and prevent growth thereof into a space between the jawbone crest and the post of said implant.

2. The method of claim 1 wherein:
    said drilling comprises drilling with a drill which produces a recess in bone crest configured to accept said subperiosteal extension; and
    said inserting said dental implant comprises locating said subperiosteal extension in said recess.

3. The method of claim 2 wherein producing a recess in bone crest configured to accept said subperiosteal extension comprises producing a recess having an asymmetric outer circumference with reference to a center axis of said hole produced by said drilling a hole.

4. The method of claim 2 wherein said recess is produced into bone crest to a depth equal to or greater than a thickness of said subperiosteal extension.

5. The method of claim 2 wherein locating said subperiosteal extension comprises locating said subperiosteal extension such that a bottom of said subperiosteal extension is snug against bone at a bottom of said recess.

6. The method of claim 2 wherein locating said subperiosteal extension comprises locating said subperiosteal extension such that a top of said subperiosteal extension is at a level of bone level adjacent to said recess.

7. The method of claim 2 wherein locating said subperiosteal extension comprises locating said subperiosteal extension such that a top of said subperiosteal extension is below a level of bone adjacent to said recess.

8. The method of claim 1 wherein said inserting said dental implant comprises positioning said subperiosteal extension to cover a gap between the post and the bone.

9. The method of claim 1 wherein:
said dental implant comprises a post and said subperiosteal extension; and
said inserting said dental implant comprises inserting said post into said hole and at the same time positioning said subperiosteal extension to cover a gap between the post and the bone.

10. The method of claim 1 wherein said covering said subperiosteal extension with said mucoperiosteal flap, including said periosteum and said gingiva, comprises guiding periosteum and gingiva onto said subperiosteal extension.

11. The method of claim 1 wherein said dental implant comprises a post and said subperiosteal extension as one piece.

12. The method according to claim 1, wherein said prosthesis is a crown.

13. The method according to claim 1, further comprising placing the prosthesis on at least a portion of the subperiosteal extension.

14. A method of preventing periosteum and gingiva from growing into a space between a jawbone crest and a dental implant, the method comprising:

elevating a mucoperiosteal flap, including periosteum and gingiva, at site of implantation;

drilling a hole in bone for inserting a dental implant comprising a subperiosteal extension and a post, the subperiosteal extension covering an entire top surface of the post, the subperiosteally extension extending radially beyond a radius of the post of said dental implant;

inserting said dental implant including said post into said hole;

attaching a prosthesis to said dental implant such that at least a portion of the prosthesis covers at least a portion of the subperiostal extension; and covering said subperiosteal extension with said mucoperiosteal flap, including periosteum, such that said periosteum and gingiva grown on said sub-periosteal extension and prevent growth thereof into a space between the jawbone crest and the post of said implant.

* * * * *